US00PP12993P2

(12) United States Plant Patent
Zary

(10) Patent No.: US PP12,993 P2
(45) Date of Patent: Sep. 24, 2002

(54) MINIATURE ROSE PLANT NAMED 'JACYARP'

(75) Inventor: Keith W. Zary, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 53 days.

(21) Appl. No.: 09/695,765

(22) Filed: Oct. 24, 2000

(51) Int. Cl.[7] ..... A01H 5/00
(52) U.S. Cl. ..... Plt./123
(58) Field of Search ..... Plt./116, 121, 122, Plt./123, 128, 129, 141, 142, 149, 150

*Primary Examiner*—Howard J. Locker
(74) *Attorney, Agent, or Firm*—Klarquist Sparkman, LLP

(57) ABSTRACT

Miniature rose plant having flowers of novel color presented in large sprays, compact rounded growth habit, dark green foliage, and ease of rooting of softwood cuttings.

1 Drawing Sheet

The present invention relates to a new and distinct variety of rose plant of the miniature class which was originated by me by crossing an unnamed seedling (not patented) with the variety JACpray (not patented).

The primary objective of this breeding was to produce a new rose variety having the bright orange-pink blend color, compact habit and healthy foliage of the female parent combined with the excellent bud form and clustering ability of the male parent. The objective was substantially achieved, along with other desirable improvements, as evidenced by the following unique combination of characteristics that are outstanding in the new variety and that distinguish it from its parents, as well as from all other varieties of which I am aware:

1. Compact, rounded plant habit;
2. Novel flower color;
3. Dark green, glossy foliage;
4. Flowers presented in large sprays; and
5. Ease of rooting from softwood cuttings.

Asexual reproduction of this new variety by cuttings, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) colour chart, except where ordinary dictionary significance of color is indicated.

Parentage:
*Seed parent*.—Unnamed seedling (not patented).
*Pollen parent*.—JACpray (not patented).

Classification:
*Botanical*.—*Rosa hybrida*.
*Commercial*.—Miniature.

FLOWER

Observations made from specimens grown in a garden environment at Somis in California, January, 1999 to August, 2000.

Blooming habit: Continuous.

Bud:

*Size*.—Half an inch long when the petals start to unfurl.

*Form*.—The bud form is long, pointed ovoid.

*Color*.—When sepals first divide, bud color is Red Group 46D on the bud tip upper third; to Red Group 47C in the middle third; and near Yellow Group 8C on the lower third. When half blown, the upper sides of the petals are Red Group 46D on the petal edge; changing to Red Group 47D from the edge to middle of the petal; and near Yellow Group 8B on the lower third of the petal. The lower sides of the petals are Red Group 46D on the petal edge, changing to Red Group 47D on the outer third of the petal and then to Yellow Group 8C on the rest of the petal.

*Sepals*.—Color: Green Group 138B with some Greyed-Purple Group 183D in areas exposed to bright sunlight. Surface texture: Covered in fine hairs. There are three lightly appendaged sepals. There are two unappendaged sepals with hairy edges.

*Receptacle*.—Color: Green Group 139B with areas of Greyed-Purple Group 183D in areas exposed to bright sunlight. Shape: Funnel. Size: Small, about ¼ inch×3/16 inch. Surface: Smooth with a few fine hairs.

*Peduncle*.—Length: Short, averaging about 1 inch. Surface: Glandular. Color: Green Group 139C. Strength: Stiff, erect, slender.

Bloom:

*Size*.—Small. Average open size is 2 inches.

*Borne*.—Several together, in pyramidal clusters of 5–9 blooms.

*Stems*.—Strength: Strong. Average length is about 6–8 inches.

*Form*.—When first open: Bloom is high centered. Permanence: Flattens, all petals curl.

*Petalage*.—Number of petals under normal conditions: 15–20.

*Color*.—The upper sides of the petals are Red Group 46D on the petal edge, changing to Red Group 47D from the petal edge to the middle of the petals; the lower third of the petals being near Yellow Group 8B. The reverse side of each petal is Red Group 46D on the petal edge, changing to Red Group 47D on the outer third of the petal, and then to Yellow Group 8D on the rest of the petal. The base of each petal has a small (⅛ inch×3/16 inch) Yellow Group 8B spot on the upper surface. The lower surface has a small (⅛ inch×3/16 inch) spot of Yellow Group 8C. The major color on the upper sides is Red Group 47D.

*Variegations*.—There are occassional streaks on the guard petals close to Green-White Group 157D.

*Discoloration*.—The general tonality at the end of the first day: No change. At the end of the third day: There is some change in overall color toward Red Group 47D on the petal edges. By day five, color fades in overall impression to Red Group 50C. Petals drop by day six.

*Fragrance*.—Slight.

Petals:

*Texture*.—Thick, leathery.

*Shape*.—Round, to deltoid.

*Form*.—Tips slightly recurved.

*Arrangement*.—Imbricated. Petaloids in the center are few (only one or two) and are Red Group 47D, sometimes with a streak of Green-White Group 157D.

*Persistence*.—Petals drop off cleanly.

*Lastingness*.—On the plant: Fair (about 5–6 days). As a cut flower: Fair (about 6 days).

Reproductive parts:

*Anthers*.—Size: Medium. Quantity: Many. Color: Yellow-Orange Group 19B. Arrangement: Regular around styles.

*Filaments*.—Color: Yellow-Orange Group 21C.

*Pollen*.—Color: Yellow-Orange Group 22A.

*Styles*.—Color: Red Group 46C.

*Stigmas*.—Color: Yellow-White Group 158A.

Plant:

*Form*.—Bush.

*Growth*.—Vigorous, upright, branching, compact. At maturity, height is 2 to 2½ feet, width is 1½ to 2 feet.

Foliage: Number of leaflets on normal mid-stem leaves: 5 or 7.

*Size*.—Small (3½ inches long×2 inches wide).

*Quantity*.—Abundant.

*Color*.—New foliage: Upper surfaces: Greyed-Orange Group 176A. Lower surfaces: Greyed-Orange Group 176B. Old foliage: Upper surface: Green Group 136A. Lower surface: Green Group 139B.

Leaflets:

*Shape*.—Pointed oval.

*Texture*.—Leathery, glossy.

*Edge*.—Serrated.

*Serration*.—Single, small.

*Petiole rachis*.—Color: Green Group 139C with some Greyed-Purple Group 183B on the upper surface, especially at the leaflet nodes.

*Petiole underside*.—Rough, with prickles.

*Stipules*.—Medium (about ½ inch), serrated, bearded.

*Disease resistance*.—Susceptible to mildew, blackspot and resistant to rust under normal growing conditions.

Wood:

*New wood*.—Color: Yellow-Green Group 146C. Bark: Smooth.

*Old wood*.—Color: Green Group 137A. Bark: Smooth.

Prickles:

*Quantity*.—On main canes from base: Ordinary. On laterals from main canes: Ordinary.

*Form*.—Short, hooked downward.

*Color when young*.—Red-Purple Group 183C.

*Color when mature*.—Greyed-Orange Group 177A.

Small prickles:

*Quantity*.—On main stalks: Few. On laterals: Many on young new shoots.

*Color*.—Young: Red-Purple Group 183C. Old: Greyed-Orange Group 177A.

I claim:

1. A new and distinct variety of rose plant of the miniature class, substantially as herein shown and described, characterized particularly by its flowers of novel color presented in large sprays, compact rounded growth habit, dark green foliage, and ease of rooting of softwood cuttings.

* * * * *

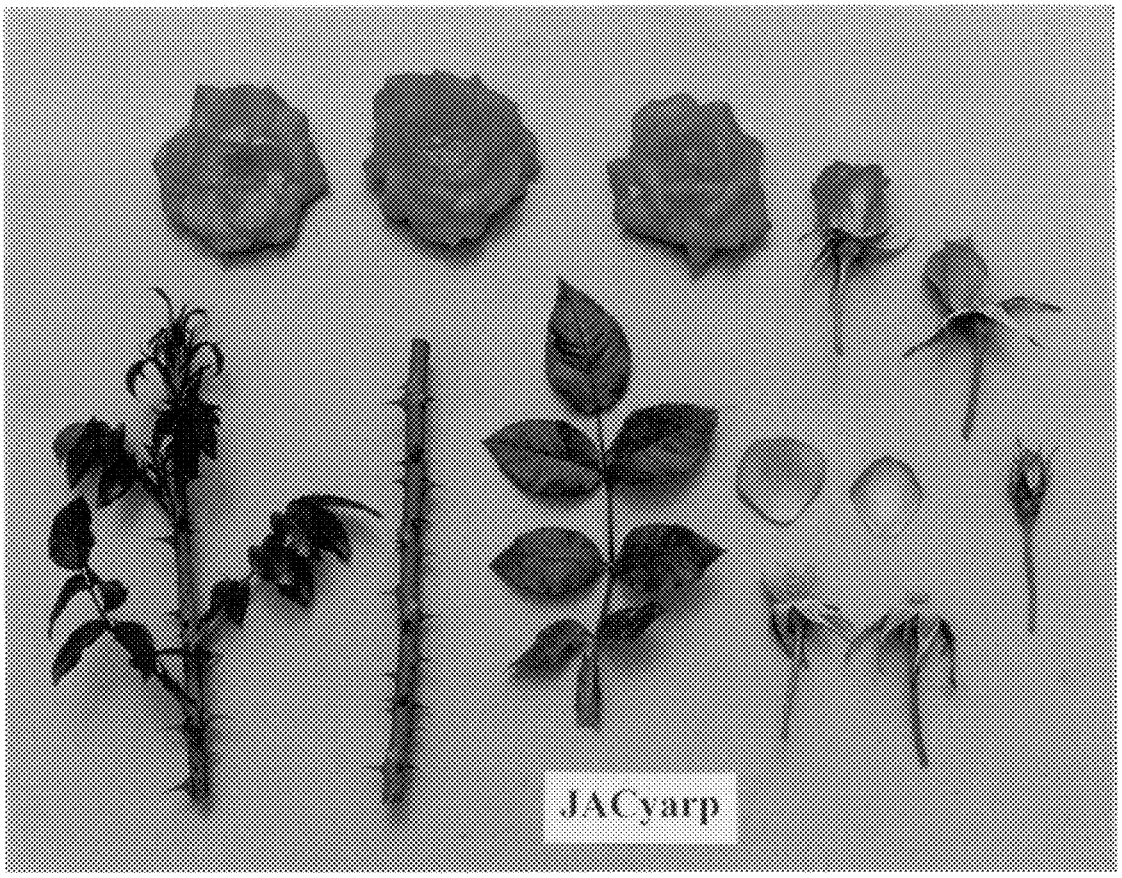
JACyarp